United States Patent
Edge

(10) Patent No.: US 9,125,894 B2
(45) Date of Patent: Sep. 8, 2015

(54) METHODS FOR PROMOTING REINNERVATION OF AUDITORY HAIR CELLS

(75) Inventor: Albert Edge, Brookline, MA (US)

(73) Assignee: Massachusetts Eye & Ear Infirmary, Boston, MA (US)

( * ) Notice: Subject to any disclaimer, the term of this patent is extended or adjusted under 35 U.S.C. 154(b) by 163 days.

(21) Appl. No.: 13/877,356

(22) PCT Filed: Sep. 29, 2011

(86) PCT No.: PCT/US2011/053868
§ 371 (c)(1),
(2), (4) Date: May 30, 2013

(87) PCT Pub. No.: WO2012/047706
PCT Pub. Date: Apr. 12, 2012

(65) Prior Publication Data
US 2013/0236477 A1 Sep. 12, 2013

Related U.S. Application Data

(60) Provisional application No. 61/390,478, filed on Oct. 6, 2010.

(51) Int. Cl.
| | |
|---|---|
| *A61K 39/395* | (2006.01) |
| *A61K 31/7088* | (2006.01) |
| *A61K 31/7105* | (2006.01) |
| *A61K 45/06* | (2006.01) |
| *A61K 31/713* | (2006.01) |
| *A61K 35/30* | (2015.01) |
| *C07K 16/22* | (2006.01) |

(52) U.S. Cl.
CPC ......... *A61K 39/3955* (2013.01); *A61K 31/7088* (2013.01); *A61K 31/713* (2013.01); *A61K 31/7105* (2013.01); *A61K 35/30* (2013.01); *A61K 45/06* (2013.01); *C07K 16/22* (2013.01); *C07K 2317/76* (2013.01)

(58) Field of Classification Search
CPC .......... A61K 2300/00; A61K 31/7088; A61K 31/7105; A61K 31/713; A61K 35/30; C07K 2317/76
USPC .................. 424/93.7, 172.1; 435/375; 514/8.4
See application file for complete search history.

(56) References Cited

PUBLICATIONS

Suda et al., Biochem. Biophys. Res. Comm., vol. 371, pp. 501-504, 2008.*
Brinks et al., "The repulsive guidance molecule RGMa is involved in the formation of afferent connections in the dentate gyms," J. Neurosci., 24:3862-3869 (2004).
Gillespie and Shepherd, "Clinical application of neurotrophic factors: the potential for primary auditory neuron protection," Eur. J. Neurosci., 22(9):2123-2133 (2005).
Matsui et al., "Caspase inhibitors promote vestibular hair cell survival and function after aminoglycoside treatment in vivo," J. Neurosci., 23(14):6111-22 (2003).
McGuinness and Shepherd, "Exogenous BDNF rescues rat spiral ganglion neurons in vivo," Otol. Neurotol., 26(5):1064-72 (2005).
Rata et al., "RGMa inhibition promotes axonal growth and recovery after spinal cord injury," J. Cell. Biol., 173(1):47-58 (2006).
Schwab et al., "Spinal cord injury-induced lesional expression of the repulsive guidance molecule (RGM)," Eur. J. Neurosci., 21(6):1569-1576 (2006).
Zheng and Gao, "Differential damage to auditory neurons and hair cells by ototoxins and neuroprotection by specific neurotrophins in rat cochlear organotypic cultures," Eur. J. Neurosci., 8:1897-1905 (1996).

* cited by examiner

*Primary Examiner* — Jeffrey Stucker
*Assistant Examiner* — Stephen Gucker
(74) *Attorney, Agent, or Firm* — Fish & Richardson P.C.

(57) ABSTRACT

This invention relates to methods for promoting reinnervation of auditory hair cells, specifically, by inhibiting Repulsive Guidance Molecule a (RGMa), a repulsive axonal guidance molecule that is expressed in the cochlea, or its receptor, neogenin.

17 Claims, 5 Drawing Sheets

METHODS FOR PROMOTING REINNERVATION OF AUDITORY HAIR CELLS

CROSS REFERENCE TO RELATED APPLICATION

This application is a U.S. National Stage Application under 35 U.S.C. 371 of International Application No. PCT/US2011/053868, filed on Sep. 29, 2011, which claims priority from U.S. Application No. 61/390,478, filed on Oct. 6, 2010, which are incorporated herein by reference in their entireties.

FEDERALLY SPONSORED RESEARCH OR DEVELOPMENT

This invention was made with Government support under Grant Nos. R01 DC007174 and P30 DC05209 awarded by the National Institute on Deafness and other Communicative Disorders (NIDCD) of the National Institutes of Health. The Government has certain rights in the invention.

TECHNICAL FIELD

This invention relates to methods for promoting reinnervation of auditory hair cells, specifically, by inhibiting Repulsive Guidance Molecule a (RGMa), a repulsive axonal guidance molecule that is expressed in the cochlea, or its receptor, neogenin.

BACKGROUND

Despite the greater capacity of peripheral as compared to central neurons to regenerate, the auditory nerve does not show spontaneous regenerative capacity (Starr et al. (2004) J Assoc Res Otolaryngol 5:411-426; White et al. (2000) Hear Res 141:12-18; McFadden et al. (2004) Brain Res 997:40-51; Kujawa and Liberman (2009) J Neurosci 29:14077-14085). The loss of afferent innervation of hair cells can result from retraction of peripheral fibers after noise damage or from complete loss of neurons (White et al. (2000) Hear Res 141: 12-18). Methods of promoting reinnervation of hair cells would therefore be important for the treatment of hearing loss.

SUMMARY

At least in part, the present invention is based on the discovery that inhibition of RGMa, a repulsive axonal guidance molecule that is expressed in the cochlea, can promote reinnervation of auditory hair cells. Thus, the present invention includes methods for the treatment of hearing loss related to loss of nerve fibers, e.g., afferent nerve fibers or of sensory neurons.

In one aspect, the invention provides methods for promoting or enhancing innervation of auditory hair cells, e.g., innervation by sensory neurons, e.g., spiral ganglion neurons and/or vestibular neurons. The methods include administering to the neurons an effective amount of one or both of an inhibitor of Repulsive Guidance Molecule a (RGMa) or an inhibitor of neogenin.

In another aspect, the invention provides methods for promoting or enhancing innervation of auditory hair cells in the inner ear of a subject in need thereof. The methods include administering to the inner ear of the subject an effective amount of one or both of an inhibitor of RGMa or an inhibitor of neogenin.

In a further aspect, the invention provides methods for treating a subject who has or is likely to have hearing loss or a balance disorder as a result of loss of or decrease in innervation of auditory hair cells. The methods include administering to the inner ear of the subject an effective amount of one or both of an inhibitor of RGMa or an inhibitor of neogenin.

In another aspect, the invention provides methods for treating a subject who has or is likely to have hearing loss as a result of loss of or decrease in auditory neurons, or a balance disorder as a result of loss of or decrease in vestibular neurons. The methods include administering to the inner ear of the subject: one or more neural progenitor cells, e.g., a neural progenitor cell that expresses nestin and Sox2, and optionally Musashi and/or Sox1; and an effective amount of one or both of an inhibitor of RGMa or an inhibitor of neogenin.

In some embodiments, the inhibitor is an inhibitory antibody or antigen-binding portion thereof that binds specifically to RGMa, an inhibitory nucleic acid that specifically reduces expression of RGMa, an inhibitory antibody or antigen-binding portion thereof that binds specifically to neogenin, or an inhibitory nucleic acid that specifically reduces expression of neogenin.

In some embodiments, the inhibitory nucleic acid is antisense or siRNA.

In some embodiments, the inhibitory antibody or antigen-binding portion thereof is an Fab or $F(ab)_2$.

In some embodiments, the methods further include administering one or more agents that promote the proliferation, differentiation, or survival or sensory neurons, e.g., caspase inhibitors, retinoic acid, Bone Morphogenetic Protein 4 (BMP4), anti-oxidants/Nrf2 activators, or neurotrophic factors such as brain-derived neurotrophic factor (BDNF), neurotrophin 3 (NT3), or NT4/5.

In some embodiments, the subject has been or will be exposed to an ototoxic level of noise or to ototoxic agents such as radiation (e.g., as part of radiotherapy for head and neck cancer); certain antibiotics (e.g., aminoglycoside antibiotics such as gentamicin and streptomycin; certain chemotherapeutic agents (e.g., cisplatin); certain anti-inflammatory drugs (e.g., sodium salicylate); heavy metals (such as lead, cadmium, or bismuth); other known or suspected ototoxic agents; or aging.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DETAILED DESCRIPTION

Figures 1A, 1B, 1C, 1D, 1E:
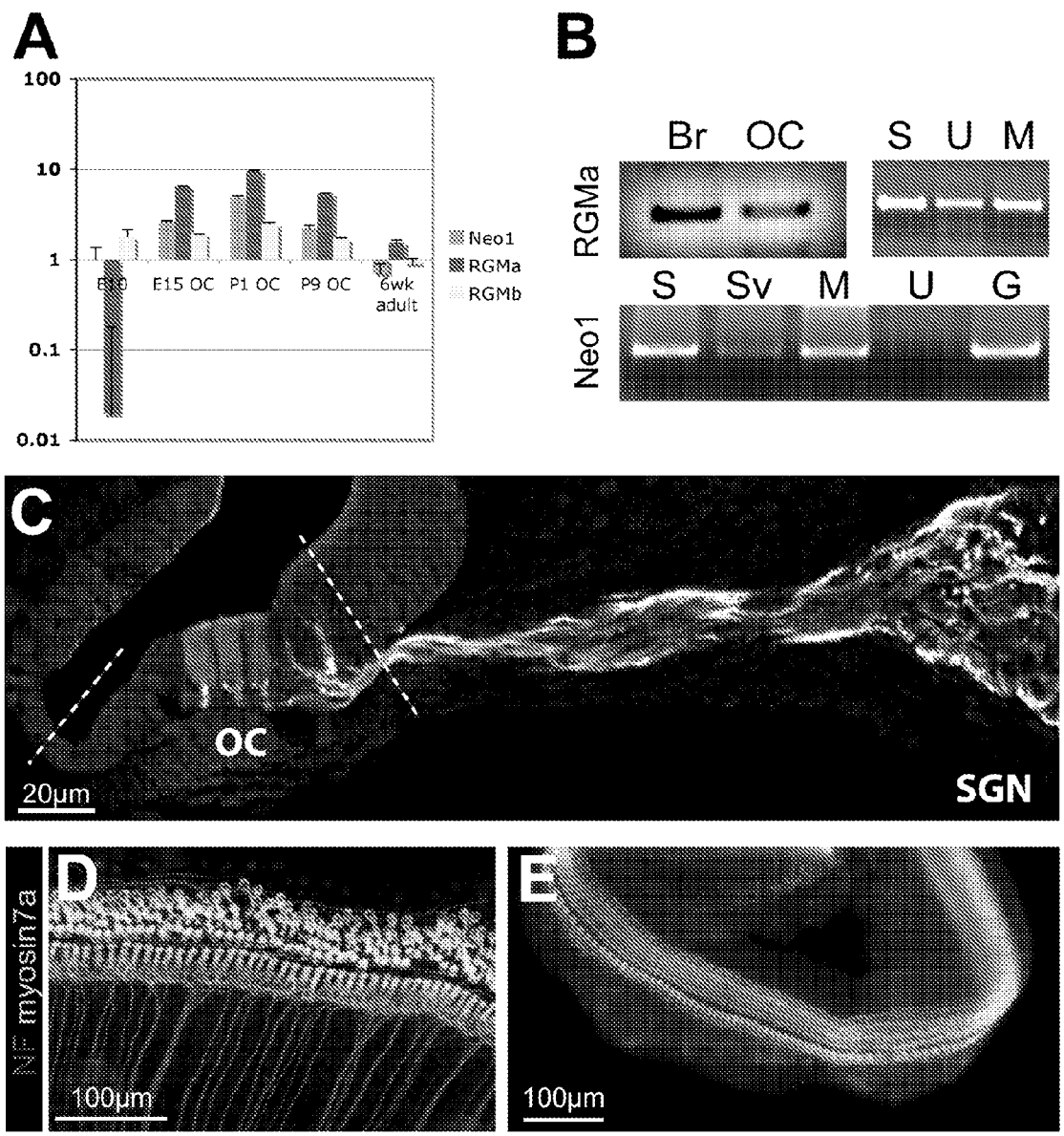
FIGS. 1A-E: Expression of guidance molecules in the cochlea. A, B RGMa, RGMb and neogenin were expressed in both the embryonic and newborn ear. RGMa expression persisted in the organ of Corti at 6 wk (A). RGMa was expressed in the cultured organ of Corti microisolate (Br: Brain; OC: organ of Corti; S: dissociated spiral ganglion; U: utricle; M: microisolate from P3 at 5 days in vitro (DIV); Sv: stria vascularis G: undissociated spiral ganglion) as well as neurons and neogenin (Neo1) was present in the spiral ganglion neurons and the intact ganglion but not in utricle (B). C The neurons were separated from the sensory epithelium by dissection indicated by the dashed lines. D, E The organ of Corti from a mouse before and after separation of the neurons was immunostained for hair cells with a myosin VIIa antibody (labeled in green, original) and for neurons with an antibody to neurofilament (labeled in red, original). Inner hair cells are innervated by the radial fibers of afferent neurons before removal of the neurons (D). After removal of the neurons, afferent innervation was lacking (E). Some neurofilament labeled remnants (in red, original) associated with the organ of Corti (tissue in E is shown immediately after dissection) degenerated within 24 hours in culture.

Regeneration of synaptic connections is an important goal for reversal of numerous diseases associated with neurodegeneration or neuronal loss, e.g., due to trauma or toxicity. Little regeneration occurs in the central nervous system, but some replacement can be achieved by transplantation (Brustle and McKay (1996) Curr Opin Neurobiol 6:688-695; Lie et al. (2004) Annu Rev Pharmacol Toxicol 44:399-421; Okano et al. (2007) J Neurochem 102:1459-1465). Peripheral nervous system axons have some limited capacity to regenerate (Sanes and Lichtman (1999) Annu Rev Neurosci 22:389-442; O'Brien et al. (2009) Curr Biol 19:2086-2090), although the environment in the adult tissue may be less favorable than in the embryo (Harel and Strittmatter (2006) Nat Rev Neurosci 7:603-616; O'Brien et al. (2009) Curr Biol 19:2086-2090; Sanes and Yamagata (2009) Annu Rev Cell Dev Biol 25:161-195; Zou et al. (2009) J Neurosci 29:7116-7123); regrowth of auditory neurons has never been clearly demonstrated (Starr et al. (2004) J Assoc Res Otolaryngol 5:411-426; Kujawa and Liberman (2009) J Neurosci 29:14077-14085). Although there is a possibility of some regeneration of afferent synapses immediately post-injury (Lerner-Natoli et al. (1997) Brain Res 749:109-119), the retraction of peripheral fibers due to noise damage results in hearing loss and a lack of fiber growth or synaptogenesis prevents spontaneous recovery (Kujawa and Liberman (2006) J Neurosci 26:2115-2123; Kujawa and Liberman (2009) J Neurosci 29:14077-14085). Motor neurons show increased ability to grow to their targets when chondroitin sulfate is removed (Curing a et al. (2007) J Neurochem 102:275-288) or antibodies to Nogo or other inhibitors of regrowth are used (Fischer et al. (2004) J Neurosci 24:1646-1651; Zhang et al. (2008) Front Biosci 13:2030-2040; Cao et al. (2010) Mol Cell Neurosci 43:1-14), and neurons that have been treated to increase axon sprouting or express synaptic molecules can show an increase in synapse formation (Fischer et al. (2004) J Neurosci 24:1646-1651; Harel and Strittmatter (2006) Nat Rev Neurosci 7:603-616; Paradis et al. (2007) Neuron 53:217-232; Cao et al. (2010) Mol Cell Neurosci 43:1-14).

New neurons contact hair cells both in vitro and in vivo in deafferented animals (Corrales et al. (2006) J Neurobiol 66:1489-1500; Martinez-Monedero et al. (2006) J Neurobiol 66:319-331; Shi et al. (2007) Eur J Neurosci 26:3016-3023; Martinez-Monedero et al. (2008) Dev Neurobiol 68:669-684). Regeneration of contacts showed that the developmental ability to contact the hair cells was maintained into adulthood. However, there appeared to be some block to complete synaptogenesis in the organ of Corti. As described herein, in the postnatal cochlea, RGMa inhibited spiral ganglion neuron sprouting and pruning, growth of fibers toward the organ of Corti and synaptogenesis. Analysis of new synapse formation between afferent neurons and hair cells postnatally thus confirmed that it plays a role as a barrier to regeneration of lost axons.

Methods of Promoting Reinnervation

The present methods are effective in promoting reinnervation of auditory hair cells, which is useful in treating hearing loss or balance disorders associated with two conditions: loss of afferent innervation, wherein the sensory neurons (e.g., spiral ganglion cells or vestibular neurons) are substantially intact; and substantial loss of sensory neurons (e.g., spiral ganglion cells or vestibular neurons).

As used in this context, to "treat" means to ameliorate at least one symptom of the disorder associated with loss or reduction of afferent innervation of hair cells. Often, deafferentation results in hearing loss; thus, a treatment can result in an improvement in hearing ability. Deafferentation can also result in balance disorders, thus, a treatment can result in an improvement in balance (i.e., lessening of symptoms associated with balance disorders, e.g., dizziness, vertigo, or a sense of imbalance). Administration of a therapeutically effective amount of a compound described herein for the treatment of a condition associated with less of innervation of auditory hair cells will result in an increase in innervation and thus improved hearing and/or balance.

In the first case, wherein some or all of the sensory neurons or vestibular neurons are still intact and viable, an improvement in hearing and/or balance is effected by promoting regrowth of neurites from the existing cells. These methods include administering to the subject, e.g., to the inner ear of the subject, a therapeutically effective amount of composition comprising an inhibitor of RGMa and/or neogenin as described herein.

In the second case, wherein the sensory neurons and/or vestibular neurons are substantially absent or non-viable, or in any case where replacement of sensory neurons and/or vestibular neurons is desirable, the methods include administering to the subject, e.g., to the inner ear of the subject, a therapeutically effective amount of a composition comprising an inhibitor of RGMa and/or neogenin as described herein, together with a population of neural progenitor cells.

The conditions may be congenital, or may be a result of disease (e.g., bacterial or viral labyrinthitis), trauma, or environmental injury, for example exposure to ototoxic levels of noise (see, e.g., Kujawa and Liberman) or ototoxic agents such as radiation (e.g., as part of radiotherapy for head and neck cancer); certain antibiotics (e.g., aminoglycoside antibiotics such as gentamicin and streptomycin (Wicke et al., Acta Otolaryngol. 85(5-6):360-2 (1978)); certain chemotherapeutic agents (e.g., cisplatin); certain anti-inflammatory drugs (e.g., sodium salicylate); heavy metals (such as lead, cadmium, or bismuth); other known or suspected ototoxic agents; or aging. See, e.g., Nadol et al., Ann Otol Rhinol Laryngol 1989; 98:411-6). The conditions may be a result of primary neural damage, e.g., action of the disease, trauma, or environmental injury directly on the neurons themselves, or a result of secondary neural loss, as a result of loss of hair cells. Thus the methods can be used to promote reinnervation in subjects who have only neural loss, or in subjects who have loss of hair cells and neurons, e.g., in conjunction with (or subsequent to) a treatment that regenerates or replaces hair cells, e.g., using cell therapy or a cochlear implant as described in US 2005/0287127, US 2007/0093878, and/or US 2007/0093878.

The inhibitors of RGMa and/or neogenin can be administered acutely, e.g., in one or a few doses, to treat or protect against a one-time exposure or injury, or can be administered chronically, e.g., to treat or protect against prolonged, repeated, or continuous exposure or injury, e.g., for subjects whose work or home environments expose them to ototoxic levels of noise or toxins.

In some embodiments, the methods include administering one or more additional agents, e.g., agents that promote the proliferation, differentiation, or survival or sensory neurons, e.g., caspase inhibitors (see, e.g., Matsui et al., J. Neurosci. 23(14):6111-22 (2003)), retinoic acid, BMP4, anti-oxidants/Nrf2 activators, or neurotrophic factors such as brain-derived neurotrophic factor (BDNF), neurotrophin 3 (NT3), or NT4/5 (McGuinness and Shepherd, Otol Neurotol. 26(5):1064-72 (2005); Gillespie and Shepherd, Eur J. Neurosci. 22(9):2123-2133 (2005); Zheng and Gao, Eur J Neurosci, 8:1897-1905 (1996)).

Anatomy and Development of the Cochlea

Spiral ganglion neurons constitute the afferent innervation of auditory hair cells, representing the first step in the ascending pathway from the cochlea (Fuchs et al. (2003) Curr Opin Neurobiol 13:452-458; Weisz et al. (2009) Nature 461:1126-1129). The afferent fibers extend from an individual synapse at the hair cell to the first central synapse in the brainstem, and the auditory pathway continues to the cortex. Hair cell synapses are glutamatergic, and presynaptic release of vesicles occurs via a ribbon synapse found in the inner ear (Glowatzki et al. (2008) Curr Opin Neurobiol 18:389-395). The hair cell synapse is well characterized and the pre and postsynaptic cells can be easily recognized. The spiral ganglion cell expresses glutamate receptors and components of the postsynaptic glutamatergic specializations such as PSD95. In addition, the synapse can be reconstituted by neurons in culture; neurons extend neurites to hair cells that had been previously denervated and express synaptic markers at points of contact (Martinez-Monedero et al. (2006) J Neurobiol 66:319-331; Martinez-Monedero et al. (2008) Dev Neurobiol 68:669-684).

The initial laying out of neuronal circuits during development requires directed growth of neurons to contact other cells in a stereotyped fashion (Tessier-Lavigne and Goodman (1996) Science 274:1123-1133; Mueller B K (1999) Annu Rev Neurosci 22:351-388; Pasterkamp and Verhaagen (2006) Philos Trans R Soc Lond B Biol Sci 361:1499-1511; Yamashita et al. (2007) Curr Opin Neurobiol 17:29-34). Axonal guidance systems are primarily expressed in the embryo, but the precise role of the individual molecules and how they give rise to the complex innervation patterns has not been completely established for the cochlea or for the peripheral nervous system. Many of the guidance molecules have limited expression after birth, and this corresponds with the time when afferent innervation of hair cells is completed in the first postnatal week (Huang et al. (2007) Development 134:2925-2933). The limited regeneration capacity of many neurons is thought to result from the loss of inherent capacity for neurite outgrowth by neurons, combined with the loss of molecules for axonal guidance in the adult (Harel and Strittmatter (2006) Nat Rev Neurosci 7:603-616; Pasterkamp and Verhaagen (2006) Philos Trans R Soc Lond B Biol Sci 361: 1499-1511; Loers and Schachner (2007) J Neurochem 101: 865-882; Zou et al. (2009) J Neurosci 29:7116-7123) and the overexpression of inhibitory molecules at the sites of damage to the mature nervous system (Fischer et al. (2004) J Neurosci 24:1646-1651; Loers and Schachner (2007) J Neurochem 101:865-882; Zhang et al. (2008) Front Biosci 13:2030-2040; Cao et al. (2010) Mol Cell Neurosci 43:1-14). There have been few studies of the importance of axonal guidance molecules in the adult (Harel and Strittmatter (2006) Nat Rev Neurosci 7:603-616; Pasterkamp and Verhaagen (2006) Philos Trans R Soc Lond B Biol Sci 361:1499-1511). The guidance molecules could act as in the embryo to aid neurons to their synaptic sites but may also prevent growth of axons to the original site. A number of axonal guidance molecules continue to be expressed in the adult, and although their role remains unclear, manipulation of these molecules has increased regrowth of neurons (Hata et al. (2006) J Cell Biol 173:47-58; Kaneko et al. (2006) Nat Med 12:1380-1389; Pasterkamp and Verhaagen (2006) Philos Trans R Soc Lond B Biol Sci 361:1499-1511).

Inhibitors of RGMa/Neogenin

The methods described herein include the administration of therapeutically effective amounts of one or more inhibitors of RGMa and/or neogenin. A number of suitable inhibitors are known in the art, including antibodies and inhibitory nucleic acids.

Repulsive Guidance Molecule a (RGMa)

RGMa is a glycosylphosphatidylinositol-anchored protein that induces growth cone collapse and plays a role in axonal pathfinding (Wilson and Key (2006) Dev Biol 296:485-498; Kyoto et al. (2007) Brain Res 1186:74-86), branching of neurites in vitro (Yoshida et al. (2008) Biochem Biophys Res Commun 372:725-729) and synaptogenesis (Kyoto et al. (2007) Brain Res 1186:74-86). A gradient of RGMa organizes projections of retinal neurons to the optic tectum in the chick (Matsunaga et al. (2006) J Neurosci 26:6082-6088; Liu et al. (2009) Biochem Biophys Res Commun 382:795-800). It is required for laminar patterning of axons in the hippocampus (Brinks et al. (2004) J Neurosci 24:3862-3869) and plays a role in the spinal cord where its inhibition led to increased neuronal projections after injury (Hata et al. (2006) J Cell Biol 173:47-58). RGMa binds to neogenin1 (Matsunaga and Chedotal (2004) Dev Growth Differ 46:481-486; Niederkofler et al. (2004) J Neurosci 24:808-818; Rajagopalan et al. (2004) Nat Cell Biol 6:756-762; Yamashita et al. (2007) Curr Opin Neurobiol 17:29-34), which is also an attractive receptor for netrin1 in Xenopus (Wilson and Key (2006) Dev Biol 296:485-498). RGMa was originally isolated as an axon guidance molecule in the visual system, but little is known about the expression and roles of RGMa and Neogenin in the adult CNS. Functional expression of RGMa in the cochlea has not previously been demonstrated.

RGMa is expressed as a number of variants, the sequences for which are given in

TABLE 1

| Isoform | Nucleic Acid | Protein | Comments |
| --- | --- | --- | --- |
| 1 | NM_001166283 | NP_001159755.1 | The longest variant. |
| 2 | NM_001166286.1 | NP_001159758.1 | Variant 2 differs in the 5' UTR, lacks a portion of the 5' coding region, and initiates translation at a downstream start codon as compared to variant 1. The encoded isoform 2 has a shorter N-terminus, compared to isoform 1. Variants 2, 3, 5 and 6 encode the same isoform 2 |
| 3 | NM_001166287.1 | NP_001159759.1 | Variant 3 differs in the 5' UTR, lacks a portion of the 5' coding region, and initiates translation at a downstream start codon, compared to variant 1. Encodes the same protein as isoform 2. |
| 4 | NM_020211.2 | NP_064596.2 | Variant (4) differs in the 5' UTR, lacks a portion of the 5' coding region, and initiates translation at an alternate start codon, compared to variant 1. The encoded isoform (3) has a distinct N-terminus and is shorter than isoform 1. |
| 5 | NM_001166288.1 | NP_001159760.1 | Variant 5 differs in the 5' UTR, lacks a portion of the 5' coding region, and initiates translation at a downstream start codon, compared to variant 1. Encodes the same protein as isoform 2. |
| 6 | NM_001166289.1 | NP_001159761.1 | Variant 6 differs in the 5' UTR, lacks a portion of the 5' coding region, and initiates translation at a downstream start codon, compared to variant 1. Encodes the same protein as isoform 2. |

Neogenin

The neogenin gene encodes a cell surface protein that is a member of the immunoglobulin superfamily, and is the receptor for RGMa. The encoded protein has four N-terminal immunoglobulin-like domains, six fibronectin type III domains, a transmembrane domain and a C-terminal internal domain that shares homology with the tumor suppressor candidate gene deleted in colorectal cancer (DCC). Alternate splicing results in multiple transcript variants.

| Isoform | Nucleic Acid | Protein | Comments |
| --- | --- | --- | --- |
| 1 | NM_002499.3 | NP_002490.2 | Neogenin isoform 1 precursor. Variant 1 represents the longest transcript and encodes the longest isoform 1. |
| 2 | NM_001172623.1 | NP_001166094.1 | Neogenin isoform 2 precursor. Variant 2 lacks an in-frame exon in the coding region, compared to variant 1. The encoded isoform 2 is shorter than isoform 1. |

-continued

| Isoform | Nucleic Acid | Protein | Comments |
|---|---|---|---|
| 3 | NM_001172624.1 | NP_001166095.1 | Neogenin isoform 3 precursor. Variant 3 lacks an in-frame exon in the coding region, compared to variant 1. The encoded isoform 3 is shorter than isoform 1. |

Antibodies

The term "antibody" as used herein refers to an immunoglobulin molecule or immunologically active portion thereof, i.e., an antigen-binding portion. Examples of immunologically active portions of immunoglobulin molecules include F(ab) and F(ab')$_2$ fragments, which retain the ability to bind antigen. Such fragments can be obtained commercially, or using methods known in the art. For example F(ab)$_2$ fragments can be generated by treating the antibody with an enzyme such as pepsin, a non-specific endopeptidase that normally produces one F(ab)$_2$ fragment and numerous small peptides of the Fc portion. The resulting F(ab)$_2$ fragment is composed of two disulfide-connected Fab units. The Fc fragment is extensively degraded and can be separated from the F(ab)$_2$ by dialysis, gel filtration or ion exchange chromatography. F(ab) fragments can be generated using papain, a non-specific thiol-endopeptidase that digests IgG molecules, in the presence of a reducing agent, into three fragments of similar size: two Fab fragments and one Fc fragment. When Fc fragments are of interest, papain is the enzyme of choice because it yields a 50,00 Dalton Fc fragment; to isolate the F(ab) fragments, the Fc fragments can be removed, e.g., by affinity purification using protein A/G. A number of kits are available commercially for generating F(ab) fragments, including the ImmunoPure IgG1 Fab and F(ab')$_2$ Preparation Kit (Pierce Biotechnology, Rockford, Ill.). In addition, commercially available services for generating antigen-binding fragments can be used, e.g., Bio Express, West Lebanon, N.H.

The antibody can be a polyclonal, monoclonal, recombinant, e.g., a chimeric, deimmunized or humanized, fully human, non-human, e.g., murine, or single chain antibody. In some embodiments the antibody has effector function and can fix complement. In some embodiments, the antibody has reduced or no ability to bind an Fc receptor. For example, the antibody can be an isotype or subtype, fragment or other mutant, which does not support binding to an Fc receptor, e.g., it has a mutagenized or deleted Fc receptor binding region. The antibody can be coupled to a toxin or imaging agent.

A number of antibodies against rGMA and neogenin are known; exemplary antibodies are described in Hata et al., J Cell Biol 173(1):47-58 (2006); Schwab et al., Eur J Neurosci 21(6):1569-1576 (2006); Brinks et al., J Neurosci 24:3862-3869 (2004). A number of antibodies are commercially available, e.g., from Abcam; Abgent; Atlas Antibodies Enzo Life Sciences, Inc.; GeneTex; GenWay Biotech, Inc; MyBioSource.com; Novus Biologicals; Proteintech Group, Inc.; R&D Systems; Sigma-Aldrich; United States Biological; and Santa Cruz Biotechnology, Inc.

Methods for making suitable antibodies are known in the art. A full-length RGMa or neogenin, or antigenic peptide fragment thereof (e.g., all or part of an extracellular domain or a fragment lacking the GPI-anchor sequence) can be used as an immunogen, or can be used to identify antibodies made with other immunogens, e.g., cells, membrane preparations, and the like, e.g., E rosette positive purified normal human peripheral T cells, as described in U.S. Pat. Nos. 4,361,549 and 4,654,210.

Methods for making monoclonal antibodies are known in the art. Basically, the process involves obtaining antibody-secreting immune cells (lymphocytes) from the spleen of a mammal (e.g., mouse) that has been previously immunized with the antigen of interest (e.g., a cancer-related antigen) either in vivo or in vitro. The antibody-secreting lymphocytes are then fused with myeloma cells or transformed cells that are capable of replicating indefinitely in cell culture, thereby producing an immortal, immunoglobulin-secreting cell line. The resulting fused cells, or hybridomas, are cultured, and the resulting colonies screened for the production of the desired monoclonal antibodies. Colonies producing such antibodies are cloned, and grown either in vivo or in vitro to produce large quantities of antibody. A description of the theoretical basis and practical methodology of fusing such cells is set forth in Kohler and Milstein, Nature 256:495 (1975), which is hereby incorporated by reference.

Mammalian lymphocytes are immunized by in vivo immunization of the animal (e.g., a mouse) with a cancer-related antigen. Such immunizations are repeated as necessary at intervals of up to several weeks to obtain a sufficient titer of antibodies. Following the last antigen boost, the animals are sacrificed and spleen cells removed.

Fusion with mammalian myeloma cells or other fusion partners capable of replicating indefinitely in cell culture is effected by known techniques, for example, using polyethylene glycol ("PEG") or other fusing agents (See Milstein and Kohler, Eur. J. Immunol. 6:511 (1976), which is hereby incorporated by reference). This immortal cell line, which is preferably murine, but can also be derived from cells of other mammalian species, including but not limited to rats and humans, is selected to be deficient in enzymes necessary for the utilization of certain nutrients, to be capable of rapid growth, and to have good fusion capability. Many such cell lines are known to those skilled in the art, and others are regularly described.

Procedures for raising polyclonal antibodies are also known. Typically, such antibodies can be raised by administering the protein or polypeptide of the present invention subcutaneously to New Zealand white rabbits that have first been bled to obtain pre-immune serum. The antigens can be injected at a total volume of 100 µl per site at six different sites. Each injected material will contain synthetic surfactant adjuvant pluronic polyols, or pulverized acrylamide gel containing the protein or polypeptide after SDS-polyacrylamide gel electrophoresis. The rabbits are then bled two weeks after the first injection and periodically boosted with the same antigen three times every six weeks. A sample of serum is then collected 10 days after each boost. Polyclonal antibodies are then recovered from the serum by affinity chromatography using the corresponding antigen to capture the antibody. Ultimately, the rabbits are euthanized, e.g., with pentobarbital 150 mg/Kg IV. This and other procedures for raising polyclonal antibodies are disclosed in E. Harlow, et al., editors, *Antibodies: A Laboratory Manual* (1988).

In addition to utilizing whole antibodies, the invention encompasses the use of binding portions of such antibodies. Such binding portions include Fab fragments, F(ab')$_2$ fragments, and Fv fragments. These antibody fragments can be made by conventional procedures, such as proteolytic fragmentation procedures, as described in J. Goding, Monoclonal Antibodies: Principles and Practice, pp. 98-118 (N.Y. Academic Press 1983).

Chimeric, humanized, de-immunized, or completely human antibodies are desirable for applications which include repeated administration, e.g., therapeutic treatment of human subjects.

Chimeric antibodies generally contain portions of two different antibodies, typically of two different species. Generally, such antibodies contain human constant regions and variable regions from another species, e.g., murine variable regions. For example, mouse/human chimeric antibodies have been reported which exhibit binding characteristics of the parental mouse antibody, and effector functions associated with the human constant region. See, e.g., Cabilly et al., U.S. Pat. No. 4,816,567; Shoemaker et al., U.S. Pat. No. 4,978,745; Beavers et al., U.S. Pat. No. 4,975,369; and Boss et al., U.S. Pat. No. 4,816,397, all of which are incorporated by reference herein. Generally, these chimeric antibodies are constructed by preparing a genomic gene library from DNA extracted from pre-existing murine hybridomas (Nishimura et al., Cancer Research, 47:999 (1987)). The library is then screened for variable region genes from both heavy and light chains exhibiting the correct antibody fragment rearrangement patterns. Alternatively, cDNA libraries are prepared from RNA extracted from the hybridomas and screened, or the variable regions are obtained by polymerase chain reaction. The cloned variable region genes are then ligated into an expression vector containing cloned cassettes of the appropriate heavy or light chain human constant region gene. The chimeric genes can then be expressed in a cell line of choice, e.g., a murine myeloma line. Such chimeric antibodies have been used in human therapy.

Humanized antibodies are known in the art. Typically, "humanization" results in an antibody that is less immunogenic, with complete retention of the antigen-binding properties of the original molecule. In order to retain all the antigen-binding properties of the original antibody, the structure of its combining-site has to be faithfully reproduced in the "humanized" version. This can potentially be achieved by transplanting the combining site of the nonhuman antibody onto a human framework, either (a) by grafting the entire nonhuman variable domains onto human constant regions to generate a chimeric antibody (Morrison et al., Proc. Natl. Acad. Sci., USA 81:6801 (1984); Morrison and Oi, Adv. Immunol. 44:65 (1988) (which preserves the ligand-binding properties, but which also retains the immunogenicity of the nonhuman variable domains); (b) by grafting only the nonhuman CDRs onto human framework and constant regions with or without retention of critical framework residues (Jones et al., Nature, 321:522 (1986); Verhoeyen et al., Science 239:1539 (1988)); or (c) by transplanting the entire nonhuman variable domains (to preserve ligand-binding properties) but also "cloaking" them with a human-like surface through judicious replacement of exposed residues (to reduce antigenicity) (Padlan, Molec. Immunol. 28:489 (1991)).

Humanization by CDR grafting typically involves transplanting only the CDRs onto human fragment onto human framework and constant regions. Theoretically, this should substantially eliminate immunogenicity (except if allotypic or idiotypic differences exist). However, it has been reported that some framework residues of the original antibody also need to be preserved (Riechmann et al., Nature 332:323 (1988); Queen et al., Proc. Natl. Acad. Sci. USA 86:10,029 (1989)). The framework residues which need to be preserved can be identified by computer modeling. Alternatively, critical framework residues may potentially be identified by comparing known antibody combining site structures (Padlan, Molec. Immun. 31(3):169-217 (1994)). The invention also includes partially humanized antibodies, in which the 6 CDRs of the heavy and light chains and a limited number of structural amino acids of the murine monoclonal antibody are grafted by recombinant technology to the CDR-depleted human IgG scaffold (Jones et al., Nature 321:522-525 (1986)).

Deimmunized antibodies are made by replacing immunogenic epitopes in the murine variable domains with benign amino acid sequences, resulting in a deimmunized variable domain. The deimmunized variable domains are linked genetically to human IgG constant domains to yield a deimmunized antibody (Biovation, Aberdeen, Scotland).

The antibody can also be a single chain antibody. A single-chain antibody (scFV) can be engineered (see, for example, Colcher et al., Ann. N.Y. Acad. Sci. 880:263-80 (1999); and Reiter, Clin. Cancer Res. 2:245-52 (1996)). The single chain antibody can be dimerized or multimerized to generate multivalent antibodies having specificities for different epitopes of the same target protein. In some embodiments, the antibody is monovalent, e.g., as described in Abbs et al., Ther. Immunol. 1(6):325-31 (1994), incorporated herein by reference.

Inhibitory Nucleic Acids

Inhibitory nucleic acids, e.g., siRNA, antisense, ribozymes, or aptamers, directed against RGMa or neogenin, can also be used.

RNA Interference

RNA interference (RNAi) is a process whereby double-stranded RNA (dsRNA) induces the sequence-specific regulation of gene expression in animal and plant cells and in bacteria (Aravin and Tuschl, FEBS Lett. 26:5830-5840 (2005); Herbert et al., Curr. Opin. Biotech. 19:500-505 (2008); Hutvagner and Zamore, Curr. Opin. Genet. Dev.:12, 225-232 (2002); Sharp, Genes Dev., 15:485-490 (2001); Valencia-Sanchez et al., Genes Dev. 20:515-524 (2006)). In mammalian cells, RNAi can be triggered by 21-nucleotide (nt) duplexes of small interfering RNA (siRNA) (Chiu et al., Mol. Cell. 10:549-561 (2002); Elbashir et al., Nature 411: 494-498 (2001)), by microRNA (miRNA), functional small-hairpin RNA (shRNA), or other dsRNAs which are expressed in vivo using DNA templates with RNA polymerase II or III promoters (Zeng et al., Mol. Cell. 9:1327-1333 (2002); Paddison et al., Genes Dev. 16:948-958 (2002); Denti, et al., Mol. Ther. 10:191-199 (2004); Lee et al., Nature Biotechnol. 20:500-505 (2002); Paul et al., Nature Biotechnol. 20:505-508 (2002); Rossi, Human Gene Ther. 19:313-317 (2008); Tuschl, T., Nature Biotechnol. 20:440-448 (2002); Yu et al., Proc. Natl. Acad. Sci. USA 99(9):6047-6052 (2002); McManus et al., RNA 8:842-850 (2002); Scherer et al., Nucleic Acids Res. 35:2620-2628 (2007); Sui et al., Proc. Natl. Acad. Sci. USA 99(6):5515-5520 (2002)).

In general, the methods described herein can use dsRNA molecules comprising 16-30, e.g., 16, 17, 18, 19, 20, 21, 22, 23, 24, 25, 26, 27, 28, 29, or 30 nucleotides in each strand, wherein one of the strands is substantially identical, e.g., at least 80% (or more, e.g., 85%, 90%, 95%, or 100%) identical, e.g., having 3, 2, 1, or 0 mismatched nucleotide(s), to a target region in the mRNA, and the other strand is complementary to the first strand. The dsRNA molecules can be chemically synthesized, or can transcribed be in vitro or in vivo, e.g., shRNA, from a DNA template. The dsRNA molecules can be designed using any method known in the art. Negative control siRNAs should not have significant sequence complementarity to the appropriate genome. Such negative controls can be designed by randomly scrambling the nucleotide sequence of the selected siRNA; a homology search can be performed to ensure that the negative control lacks homology to any other gene in the appropriate genome. In addition, negative control siRNAs can be designed by introducing one or more base mismatches into the sequence.

siRNA against RGMa and neogenin have been previously described; see, e.g., Matsunaga and Chedotal, Develop. Growth Differ 46:481-486 (2004); Matsunaga et al., Nat Cell Biol 6:749-755 (2004); and Matsunaga et al., J. Neurosci 26(22):6082-6088 (2006). In addition, siRNAs against RGMa and neogenin are commercially available, e.g., from Abnova Corporation; Novus Biologicals; Open Biosystems, now sold as Thermo Scientific; OriGene Technologies; Santa Cruz Biotechnology, Inc.; and Sigma-Aldrich.

The methods described herein can use both siRNA and modified siRNA derivatives, e.g., siRNAs modified to alter a property such as the specificity and/or pharmacokinetics of the composition, for example, to increase half-life in the body, e.g., crosslinked siRNAs. Thus, the invention includes methods of administering siRNA derivatives that include siRNA having two complementary strands of nucleic acid, such that the two strands are crosslinked. The oligonucleotide modifications include, but are not limited to, 2'-O-methyl, 2'-fluoro, 2'-O-methyoxyethyl and phosphorothioate, boranophosphate, 4'-thioribose. (Wilson and Keefe, Curr. Opin. Chem. Biol. 10:607-614 (2006); Prakash et al., J. Med. Chem. 48:4247-4253 (2005); Soutschek et al., Nature 432:173-178 (2004)).

In some embodiments, the siRNA derivative has at its 3' terminus a biotin molecule (e.g., a photocleavable biotin), a peptide (e.g., a Tat peptide), a nanoparticle, a peptidomimetic, organic compounds (e.g., a dye such as a fluorescent dye), or dendrimer. Modifying siRNA derivatives in this way may improve cellular uptake or enhance cellular targeting activities of the resulting siRNA derivative as compared to the corresponding siRNA, are useful for tracing the siRNA derivative in the cell, or improve the stability of the siRNA derivative compared to the corresponding siRNA.

The inhibitory nucleic acid compositions can be unconjugated or can be conjugated to another moiety, such as a nanoparticle, to enhance a property of the compositions, e.g., a pharmacokinetic parameter such as absorption, efficacy, bioavailability, and/or half-life. The conjugation can be accomplished by methods known in the art, e.g., using the methods of Lambert et al., Drug Deliv. Rev.:47(1), 99-112 (2001) (describes nucleic acids loaded to polyalkylcyanoacrylate (PACA) nanoparticles); Fattal et al., J. Control Release 53(1-3):137-43 (1998) (describes nucleic acids bound to nanoparticles); Schwab et al., Ann. Oncol. 5 Suppl. 4:55-8 (1994) (describes nucleic acids linked to intercalating agents, hydrophobic groups, polycations or PACA nanoparticles); and Godard et al., Eur. J. Biochem. 232(2):404-10 (1995) (describes nucleic acids linked to nanoparticles). The inhibitory nucleic acid molecules can also be labeled using any method known in the art; for instance, the nucleic acid compositions can be labeled with a fluorophore, e.g., Cy3, fluorescein, or rhodamine. The labeling can be carried out using a kit, e.g., the SILENCER™ siRNA labeling kit (Ambion). Additionally, the siRNA can be radiolabeled, e.g., using $^3$H, $^{32}$P, or other appropriate isotope.

siRNA delivery

Direct delivery of siRNA in saline or other excipients can silence target genes in tissues, such as the eye, lung, and central nervous system (Bitko et al., Nat. Med. 11:50-55 (2005); Shen et al., Gene Ther. 13:225-234 (2006); Thakker, et al., Proc. Natl. Acad. Sci. U.S.A. (2004)). In adult mice, efficient delivery of siRNA can be accomplished by "high-pressure" delivery technique, a rapid injection (within 5 seconds) of a large volume of siRNA containing solution into animal via the tail vein (Liu (1999), supra; McCaffrey (2002), supra; Lewis, Nature Genetics 32:107-108 (2002)).

Liposomes and nanoparticles can also be used to deliver siRNA into animals. Delivery methods using liposomes, e.g., stable nucleic acid-lipid particles (SNALPs), dioleoyl phosphatidylcholine (DOPC)-based delivery system, as well as lipoplexes, e.g., Lipofectamine 2000, TransIT-TKO, have been shown to effectively repress target mRNA (de Fougerolles, Human Gene Ther. 19:125-132 (2008); Landen et al., Cancer Res. 65:6910-6918 (2005); Luo et al., Mol. Pain. 1:29 (2005); Zimmermann et al., Nature 441:111-114 (2006)). Conjugating siRNA to peptides, RNA aptamers, antibodies, or polymers, e.g., dynamic polyconjugates, cyclodextrin-based nanoparticles, atelocollagen, and chitosan, can improve siRNA stability and/or uptake. (Howard et al., Mol. Ther. 14:476-484 (2006); Hu-Lieskovan et al., Cancer Res. 65:8984-8992 (2005); Kumar, et al., Nature 448:39-43; McNamara et al., Nat. Biotechnol. 24:1005-1015 (2007); Rozema et al., Proc. Natl. Acad. Sci. U.S.A. 104:12982-12987 (2007); Song et al., Nat. Biotechnol. 23:709-717 (2005); Soutschek (2004), supra; Wolfrum et al., Nat. Biotechnol. 25:1149-1157 (2007)).

Viral-mediated delivery mechanisms can also be used to induce specific silencing of targeted genes through expression of siRNA, for example, by generating recombinant adenoviruses harboring siRNA under RNA Pol II promoter transcription control (Xia et al. (2002), supra). Infection of HeLa cells by these recombinant adenoviruses allows for diminished endogenous target gene expression. Injection of the recombinant adenovirus vectors into transgenic mice expressing the target genes of the siRNA results in in vivo reduction of target gene expression. Id. In an animal model, whole-embryo electroporation can efficiently deliver synthetic siRNA into post-implantation mouse embryos (Calegari et al., Proc. Natl. Acad. Sci. USA 99(22):14236-40 (2002)).

Stable siRNA Expression

Synthetic siRNAs can be delivered into cells, e.g., by direct delivery, cationic liposome transfection, and electroporation. However, these exogenous siRNA typically only show short term persistence of the silencing effect (4-5 days). Several strategies for expressing siRNA duplexes within cells from recombinant DNA constructs allow longer-term target gene suppression in cells, including mammalian Pol II and III promoter systems (e.g., H1, U1, or U6/snRNA promoter systems (Denti et al. (2004), supra; Tuschl (2002), supra); capable of expressing functional double-stranded siRNAs (Bagella et al., J. Cell. Physiol. 177:206-213 (1998); Lee et al. (2002), supra; Miyagishi et al. (2002), supra; Paul et al. (2002), supra; Scherer et al. (2007), supra; Yu et al. (2002), supra; Sui et al. (2002), supra).

Transcriptional termination by RNA Pol III occurs at runs of four consecutive T residues in the DNA template, providing a mechanism to end the siRNA transcript at a specific sequence. The siRNA is complementary to the sequence of the target gene in 5'-3' and 3'-5' orientations, and the two strands of the siRNA can be expressed in the same construct or in separate constructs. Hairpin siRNAs, driven by H1 or U6 snRNA promoter and expressed in cells, can inhibit target gene expression (Bagella et al. (1998), supra; Lee et al. (2002), supra; Miyagishi et al. (2002), supra; Paul et al. (2002), supra; Yu et al. (2002), supra; Sui et al. (2002) supra). Constructs containing siRNA sequence under the control of T7 promoter also make functional siRNAs when cotransfected into the cells with a vector expression T7 RNA polymerase (Jacque (2002), supra).

In another embodiment, siRNAs can be expressed in a miRNA backbone which can be transcribed by either RNA Pol II or III. MicroRNAs are endogenous noncoding RNAs of approximately 22 nucleotides in animals and plants that can post-transcriptionally regulate gene expression (Bartel, Cell 116:281-297 (2004); Valencia-Sanchez et al., Genes & Dev. 20:515-524 (2006)) One common feature of miRNAs is that they are excised from an approximately 70 nucleotide precursor RNA stem loop by Dicer, an RNase III enzyme, or a homolog thereof. By substituting the stem sequences of the miRNA precursor with the sequence complementary to the target mRNA, a vector construct can be designed to produce siRNAs to initiate RNAi against specific mRNA targets in mammalian cells. When expressed by DNA vectors containing polymerase II or III promoters, miRNA designed hairpins can silence gene expression (McManus (2002), supra; Zeng (2002), supra).

Uses of Engineered RNA Precursors to Induce RNAi

Engineered RNA precursors, introduced into cells or whole organisms as described herein, will lead to the production of a desired siRNA molecule. Such an siRNA molecule will then associate with endogenous protein components of the RNAi pathway to bind to and target a specific mRNA sequence for cleavage, destabilization, and/or translation inhibition destruction. In this fashion, the mRNA to be targeted by the siRNA generated from the engineered RNA precursor will be depleted from the cell or organism, leading to a decrease in the concentration of the protein encoded by that mRNA in the cell or organism.

Antisense

An "antisense" nucleic acid can include a nucleotide sequence that is complementary to a "sense" nucleic acid encoding a protein, e.g., complementary to the coding strand of a double-stranded cDNA molecule or complementary to a target mRNA sequence. The antisense nucleic acid can be complementary to an entire coding strand of a target sequence, or to only a portion thereof (for example, the coding region of a target gene). In another embodiment, the antisense nucleic acid molecule is antisense to a "noncoding region" of the coding strand of a nucleotide sequence encoding the selected target gene (e.g., the 5' and 3' untranslated regions).

An antisense nucleic acid can be designed such that it is complementary to the entire coding region of a target mRNA but can also be an oligonucleotide that is antisense to only a portion of the coding or noncoding region of the target mRNA. For example, the antisense oligonucleotide can be complementary to the region surrounding the translation start site of the target mRNA, e.g., between the −10 and +10 regions of the target gene nucleotide sequence of interest. An antisense oligonucleotide can be, for example, about 7, 10, 15, 20, 25, 30, 35, 40, 45, 50, 55, 60, 65, 70, 75, 80, or more nucleotides in length.

An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used.

The antisense nucleic acid also can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

Based upon the sequences disclosed herein, one of skill in the art can easily choose and synthesize any of a number of appropriate antisense molecules for use in accordance with the present invention. For example, a "gene walk" comprising a series of oligonucleotides of 15-30 nucleotides spanning the length of a target nucleic acid can be prepared, followed by testing for inhibition of target gene expression. Optionally, gaps of 5-10 nucleotides can be left between the oligonucleotides to reduce the number of oligonucleotides synthesized and tested.

The antisense nucleic acid molecules of the invention are typically administered to a subject (e.g., by direct injection at a tissue site), or generated in situ such that they hybridize with or bind to cellular mRNA and/or genomic DNA encoding a target protein to thereby inhibit expression of the protein, e.g., by inhibiting transcription, splicing, and/or translation. Alternatively, antisense nucleic acid molecules can be modified to target selected cells and then administered systemically. For systemic administration, antisense molecules can be modified such that they specifically bind to receptors or antigens expressed on a selected cell surface, e.g., by linking the antisense nucleic acid molecules to peptides or antibodies that bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter can be used.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al., Nucleic Acids. Res. 15:6625-6641 (1987)). The antisense nucleic acid molecule can also comprise a 2'-O-methylribonucleotide (Inoue et al., Nucleic Acids Res. 15:6131-6148 (1987)), 2'-O-methoxyethylribonucleotide, locked nucleic acid, ethylene-bridged nucleic acid, oxetane-modified ribose, peptide nucleic acid, or a chimeric RNA-DNA analogue (Inoue et al., FEBS Lett., 215:327-330 (1987)).

In some embodiments, the antisense nucleic acid is a morpholino oligonucleotide (see, e.g., Heasman, Dev. Biol. 243: 209-14 (2002); Iversen, Curr. Opin. Mol. Ther. 3:235-8 (2001); Summerton, Biochim. Biophys. Acta. 1489:141-58 (1999).

Target gene expression can be inhibited by targeting nucleotide sequences complementary to a regulatory region, e.g., promoters and/or enhancers) to form triple helical structures that prevent transcription of the target gene in target cells. See generally, Helene, Anticancer Drug Des. 6:569-84 (1991); Helene, Ann. N.Y. Acad. Sci. 660:27-36 (1992); and Maher, Bioassays 14:807-15 (1992). The potential sequences that can be targeted for triple helix formation can be increased by creating a so called "switchback" nucleic acid molecule.

Switchback molecules are synthesized in an alternating 5'-3', 3'-5' manner, such that they base pair with first one strand of a duplex and then the other, eliminating the necessity for a sizeable stretch of either purines or pyrimidines to be present on one strand of a duplex.

Ribozymes

Ribozymes are a type of RNA that can be engineered to enzymatically cleave and inactivate other RNA targets in a specific, sequence-dependent fashion. By cleaving the target RNA, ribozymes inhibit translation, thus preventing the expression of the target gene. Ribozymes can be chemically synthesized in the laboratory and structurally modified to increase their stability and catalytic activity using methods known in the art. Alternatively, ribozyme genes can be introduced into cells through gene-delivery mechanisms known in the art. A ribozyme having specificity for a target-protein encoding nucleic acid can include one or more sequences complementary to the nucleotide sequence of a target cDNA disclosed herein, and a sequence having known catalytic sequence responsible for mRNA cleavage (see U.S. Pat. No. 5,093,246 or Haselhoff and Gerlach Nature 334:585-591 (1988)). For example, a derivative of a Tetrahymena L-19 IVS RNA can be constructed in which the nucleotide sequence of the active site is complementary to the nucleotide sequence to be cleaved in a target mRNA. See, e.g., Cech et al., U.S. Pat. No. 4,987,071; and Cech et al., U.S. Pat. No. 5,116,742. Alternatively, a target mRNA can be used to select a catalytic RNA having a specific ribonuclease activity from a pool of RNA molecules. See, e.g., Bartel and Szostak, Science 261: 1411-1418 (1993).

Pharmaceutical Compositions and Methods of Administration

The methods described herein include the manufacture and use of pharmaceutical compositions, which include inhibitors described herein as active ingredients. Also included are the pharmaceutical compositions themselves.

Pharmaceutical compositions typically include a pharmaceutically acceptable carrier. As used herein the language "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions, e.g., as described herein.

Pharmaceutical compositions are typically formulated to be compatible with its intended route of administration. Examples of routes of administration include parenteral, e.g., intravenous, intradermal, subcutaneous, oral (e.g., inhalation), transdermal (topical), transmucosal, and rectal administration.

Methods of formulating suitable pharmaceutical compositions are known in the art, see, e.g., *Remington: The Science and Practice of Pharmacy*, 21st ed., 2005; and the books in the series *Drugs and the Pharmaceutical Sciences: a Series of Textbooks and Monographs* (Dekker, NY). For example, solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use can include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yield a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds can be delivered in the form of an aerosol spray from a pressured container or dispenser that contains a suitable propellant, e.g., a gas such as carbon dioxide, or a nebulizer. Such methods include those described in U.S. Pat. No. 6,468,798.

Systemic administration of a therapeutic compound as described herein can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The pharmaceutical compositions can also be prepared in the form of suppositories (e.g., with conventional suppository bases such as cocoa butter and other glycerides) or retention enemas for rectal delivery.

Therapeutic compounds that are or include nucleic acids can be administered by any method suitable for administration of nucleic acid agents, such as a DNA vaccine. These methods include gene guns, bio injectors, and skin patches as well as needle-free methods such as the micro-particle DNA vaccine technology disclosed in U.S. Pat. No. 6,194,389, and the mammalian transdermal needle-free vaccination with powder-form vaccine as disclosed in U.S. Pat. No. 6,168,587. Additionally, intranasal delivery is possible, as described in, inter alia, Hamajima et al., Clin. Immunol. Immunopathol., 88(2), 205-10 (1998). Liposomes (e.g., as described in U.S. Pat. No. 6,472,375) and microencapsulation can also be used. Biodegradable targetable microparticle delivery systems can also be used (e.g., as described in U.S. Pat. No. 6,471,996).

In one embodiment, the therapeutic compounds are prepared with carriers that will protect the therapeutic compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques, or obtained commercially, e.g., from Alza Corporation and Nova Pharmaceuticals, Inc. Liposomal suspensions (including liposomes targeted to selected cells with monoclonal antibodies to cellular antigens) can also be used as pharmaceutically acceptable carriers. These can be prepared according to methods known to those skilled in the art, for example, as described in U.S. Pat. No. 4,522,811.

The pharmaceutical compositions can be included in a container, pack, or dispenser together with instructions for administration.

Neural Progenitor Cells

In subjects who have some loss of sensory neural cells, e.g., spiral ganglion cells, the present methods may further include the administration of a population of neural progenitor cells, to regenerate the lost neural cells. For example, the methods may include administering a substantially pure population of nestin- and Sox-2 expressing neural progenitor cells, e.g., as described in US 2005/0287127 and US 2007/0093878, and in Martinez-Monedero et al. (2006) J Neurobiol 66:319-331; Martinez-Monedero et al. (2008) Dev Neurobiol 68:669-684; and Shi et al. (2007) Eur J Neurosci 26:3016-3023. The neural progenitor cells can be obtained by any of a number of methods, including isolation of inner ear progenitor cells (e.g., from the subject or a matched donor, e.g., a cadaver), or by generation of inner ear progenitor cells from stem or pluripotent cells, e.g., embryonic stem (ES) cells, induced pluripotent stem (iPS) cells. In some embodiments, the stem cells are adult stem cells, e.g., adult stem cells are derived from the inner ear, bone marrow, mesenchyme, skin, fat, liver, muscle, or blood, or embryonic stem cells or stem cells obtained from a placenta or umbilical cord. In some embodiments, the progenitor cells are derived from the inner ear, bone marrow, mesenchyme, skin, fat, liver, muscle, or blood.

In some embodiments, administering the population of cells comprises (a) injecting the cells into the luminae of the cochlea, into the auditory nerve trunk in the internal auditory meatus, or into the scala tympani or (b) implanting the cells within a cochlea implant. See, e.g., US 2005/0287127 and US 2007/0093878.

EXAMPLES

The invention is further described in the following examples, which do not limit the scope of the invention described in the claims.

Example 1

Replacement of Afferent Innervation of Hair Cells by Newborn Spiral Ganglion Neurons after Hair Cell Denervation Organ of Corti explants were obtained and maintained as follows. In all cultures, cells were maintained in growth medium: DMEM: F-12 (Gibco) supplemented with B27 and N2 supplements (Gibco), and 10% fetal bovine serum (Gibco). Cultures were maintained at 37° C. in a humidified incubator with 5% $CO_2$. In all experiments, the media was supplemented with 50 ng/ml NT-3 (Chemicon) and 10 ng/ml BDNF (Chemicon) after the tissue isolation and plating. For the co-cultures, spiral ganglion neurons were trypsinized and dissociated after dissection from P3-5 mouse cochlea as described previously (Flores-Otero et al. (2007) J Neurosci 27:14023-14034) (Martinez-Monedero et al. (2006) J Neurobiol 66:319-331; Martinez-Monedero et al. (2008) Dev Neurobiol 68:669-684Martinez-Monedero et al., 2006). The cells were cultured overnight in DMEM: F-12 (Gibco) supplemented with B27 and N2 supplements (Gibco) and were then collected by centrifugation. The resulting cells were triturated to a single-cell suspension and the neurons from two ears were used in a well of a 4-well plate containing two organ of Corti explants.

These explant cultures provide a well defined system in which to assess the influence of various factors on the formation of synapses. Inner and outer hair cells were carefully dissected along with their surrounding supporting cells and plated on a coated (laminin, 50 µg/ml; BD Biosciences, poly-L-ornithine, 0.01%; Sigma) cover glass in 4-well plates (Greiner) overnight in a $CO_2$ incubator. The hair cells were removed as an intact alignment of a single row of inner hair cells and three rows of outer hair cells by cutting the auditory nerve fibers at the level of the spiral lamina. By separating the tissue this way, we were able to eliminate all pre-existing connections. Neurons were randomly placed around the organ of Corti. For the RGMa treatment, anti-rat RGMa (10 µg/ml; IBL) was added to the culture medium. These cultures were used between 4 and 21 days in vitro (DIV) to allow the appropriate amount of time for neuronal processes to grow to the explants and re-form connections.

Immunofluorescence

For immunofluorescence microscopy, cultures were fixed with 4% paraformaldehyde at room temperature, followed by 0.1% Triton X-100 and 15% normal goat serum at RT for 1 hour for permeabilization and blocking Primary antibodies—anti-CtBP2 (mouse monoclonal IgG1; BD Biosciences), anti-PSD95 (mouse monoclonal IgG2a, NeuroMab), anti-neurofilament heavy chain (chicken polyclonal; Chemicon) and anti-myosin VIIa (rabbit polyclonal; Proteus)—were applied and incubated overnight at 4° C. After rinsing three times for 10 min with 0.01 M PBS, pH 7.4, co-cultures were incubated with one of the following secondary antibodies for 1 hour at room temperature: Cyanine-5-conjugated goat anti-mouse IgG1 (Caltad Laboratories), biotin-conjugated goat anti-mouse IgG2a (Caltad Laboratories), Alexa 568-Streptavidin (Molecular Probes), Alexa Fluor 488 goat anti-chicken (Molecular Probes) or Alexa 350 goat anti-rabbit (Molecular Probes). Finally, after three PBS rinses, cultures were placed onto a glass microscope slide with a drop of fluorescent mounting medium (DakoCytomation), mounted with Dako fluorescent mounting medium (Dako) and viewed using a Leica confocal microscope. Images were analyzed with Metamorph software and processed with Adobe Photoshop. Triple labeling CtBP2-PSD95 associated with neurofilament was counted in all cultures for quantification and statistical analysis was done using Sigma Plot software. Significance was determined by the Mann Whitney test ($*p<0.05$).

Example 2

Screen for Inhibitory Molecules

As a part of an effort to define the axonal guidance molecules expressed in the developing inner ear, a screen was performed for molecules that could play a role in adult in preventing axonal regeneration in the sensory organs of the ear. Quantitative RT-PCR was used to assess expression of candidate guidance molecules in embryonic inner ear. RGMa, which has not previously been described in the auditory system, was expressed during development of the cochlea and continued to be expressed after birth (FIG. 1A), an exception to the generally observed expression of many guidance molecules exclusively in development. For comparison, two other family members that were expressed during development, RGMb and neogenin, were assessed and found to be present at low levels in the mature inner ear.

RGMa expression could be seen in P9 organ of Corti and brain (FIG. 1B). Within the inner ear it was expressed in organ of Corti and utricle as well as the spiral ganglion based on RT-PCR. The antibody to RGMa could not accurately localize the protein, although staining was seen in cells near the basilar membrane and in the spiral ganglion. When neurons were separated from the sensory cells of organ of Corti (FIG. 1C) to prepare a microisolate (FIG. 1D) followed by 5 days in culture, during which the endings of neurons were completely lost (FIG. 1E), RGMa was not lost from the organ of Corti (FIG. 1B, RGMa). Thus, RGMa is expressed in the organ of Corti where peripheral fibers extended from regenerating afferents could contact RGMa and be repelled. The RGMa receptor, neogenin, was expressed in neurons, and in the microisolate of organ of Corti, but not in utricle based on RT-PCR (FIG. 1B, Neo1) and immunostaining.

Example 3

Effect of RGMa on Growth of Fibers to the Organ of Corti

Figures 2A, 2B, 2C, 2D, 2E, 2F:
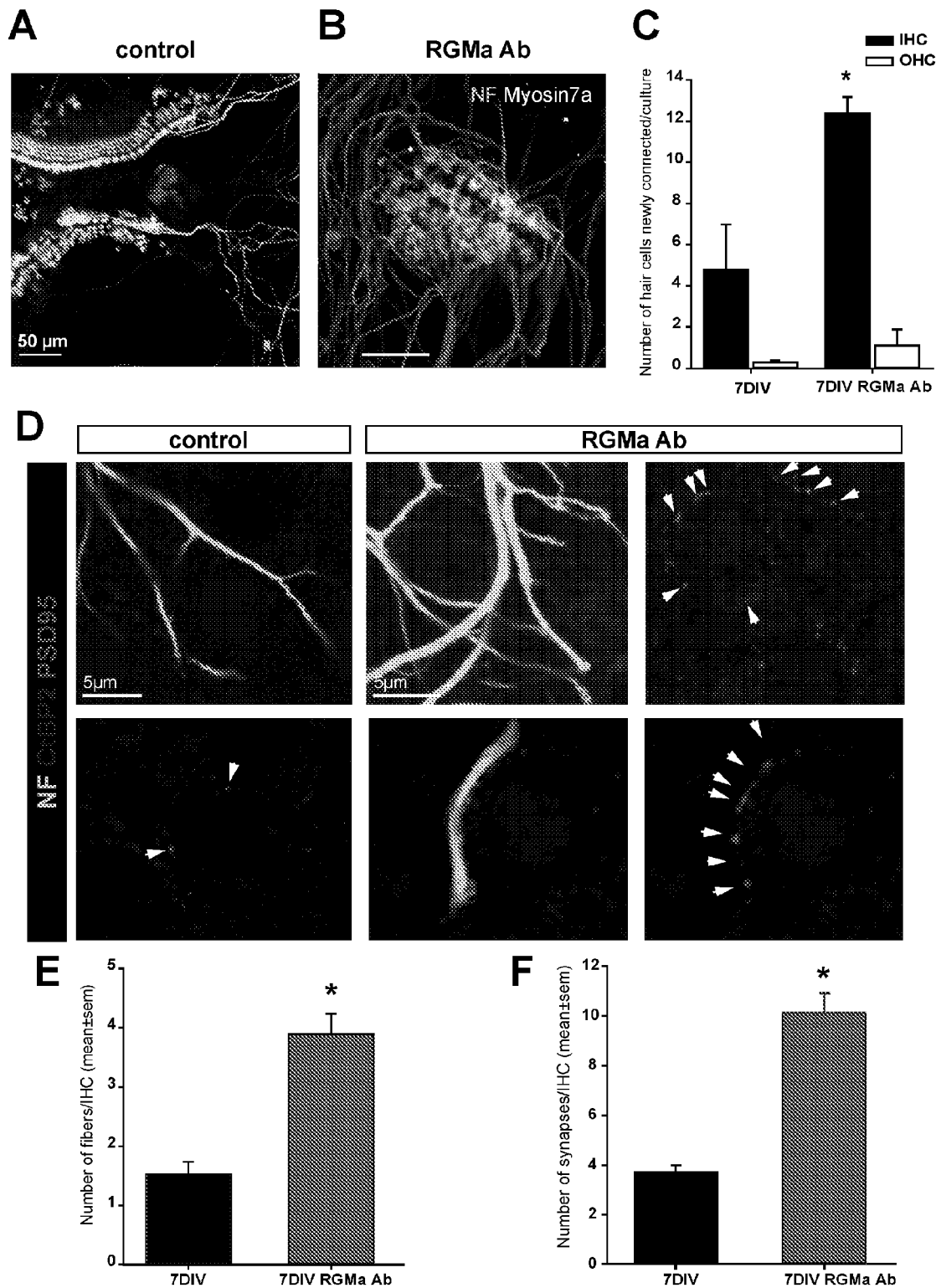
FIGS. 2A-F: Inhibition of RGMa increased growth of fibers and innervation of hair cells. A-C Ingrowth of neurons to the de-afferented organ of Corti in culture was observed for spiral ganglion neurons (A), but treatment (B) with an antibody against RGMa (RGMa Ab) increased sprouting and growth of spiral ganglion neurons to hair cells (C). Scale bar, 50 μM in A and B. D-F Inhibition of RGMa resulted in an increase in both the number of fibers that grew to hair cells and the number of synapses. New synapses were quantified at day 7 of the cultures immunostained with neurofilament (NF, green, original), PSD95 (red, original) and CtBP2 (blue, original) in the absence (control, top and bottom shown with and without neurofilament to reveal the synapses) or presence (RGMa Ab, images shown with and without neurofilament to reveal the synapses) of RGMa antibody. CtBP2-PSD95-labeled synapses that had closely adjacent staining (indicated by the white arrowheads) were counted and were readily distinguishable from occasional background staining in the cytoplasm for PSD95. The number of fibers contacting each inner hair cell (1HC) at 7 days in vitro (E) and the number of synapses per inner hair cell (F) were increased in cultures treated with the antibody. Asterisks indicate significance ($p<0.05$).

To test the effect of RGMa on the reinnervation of hair cells, the microisolate of the organ of Corti was used as a target for new neurons and the growth of fibers to the hair cells was assessed. When spiral ganglion neurons dissociated at birth were placed in the culture in close proximity to the organ of Corti, new fibers were extended and contacted cells in the organ of Corti (FIG. 2A). Blocking RGMa with an antibody led to an increase in growth of fibers (FIG. 2B) and resulted in a significant increase in the number of hair cells contacted by fibers from the newborn spiral ganglion neurons. Quantitative measurements revealed an increase in the number of contacts with both inner and outer hair cells in the antibody-treated as compared to control organ of Corti; the number increased from $4.77\pm2.20$ (n=11) in the control to $12.37\pm0.80$ (n=156) in the antibody-treated cultures for the inner hair cells (n=inner hair cells counted; 3 separate experiments; FIG. 2C).

Innervation as measured by fiber ingrowth was dramatically increased when the antibody to RGMa was added to the cultured microisolates (FIGS. 2D, E). To determine whether the additional fiber ingrowth resulted in an increased rate of synapse formation with the RGMa antibody-treated hair cells, the number of synapses with hair cells were evaluated by assessment of the pre- and postsynaptic densities. We chose to stain for the postsynaptic densities with an antibody to PSD95, a component of the postsynaptic density, and for the ribbon synapse with an antibody to CtBP2, which stains the ribbon protein, ribeye. Innervation of hair cells by spiral ganglion neurons resulted in the close apposition of the afferent endings (PSD95) to the hair cell ribbons (CtBP2), thus marking the synapses from both sides (FIG. 2D). Some of the ribbons were clearly involved in synapses with the fibers whereas others were unoccupied. The synapses co-localized with neurofilament antibody-positive fibers (synapses with hair cells shown in FIG. 2D) and were sharply increased by addition of the antibody against RGMa. The number of synapses per inner hair cell increased from $3.71\pm0.28\%$ (n=38) in the control to $10.12\pm0.80\%$ (n=157) in the antibody treated cultures (n=inner hair cells counted; 3 separate experiments; FIG. 2F).

Example 4

Figures 3A, 3B, 3C, 3D:
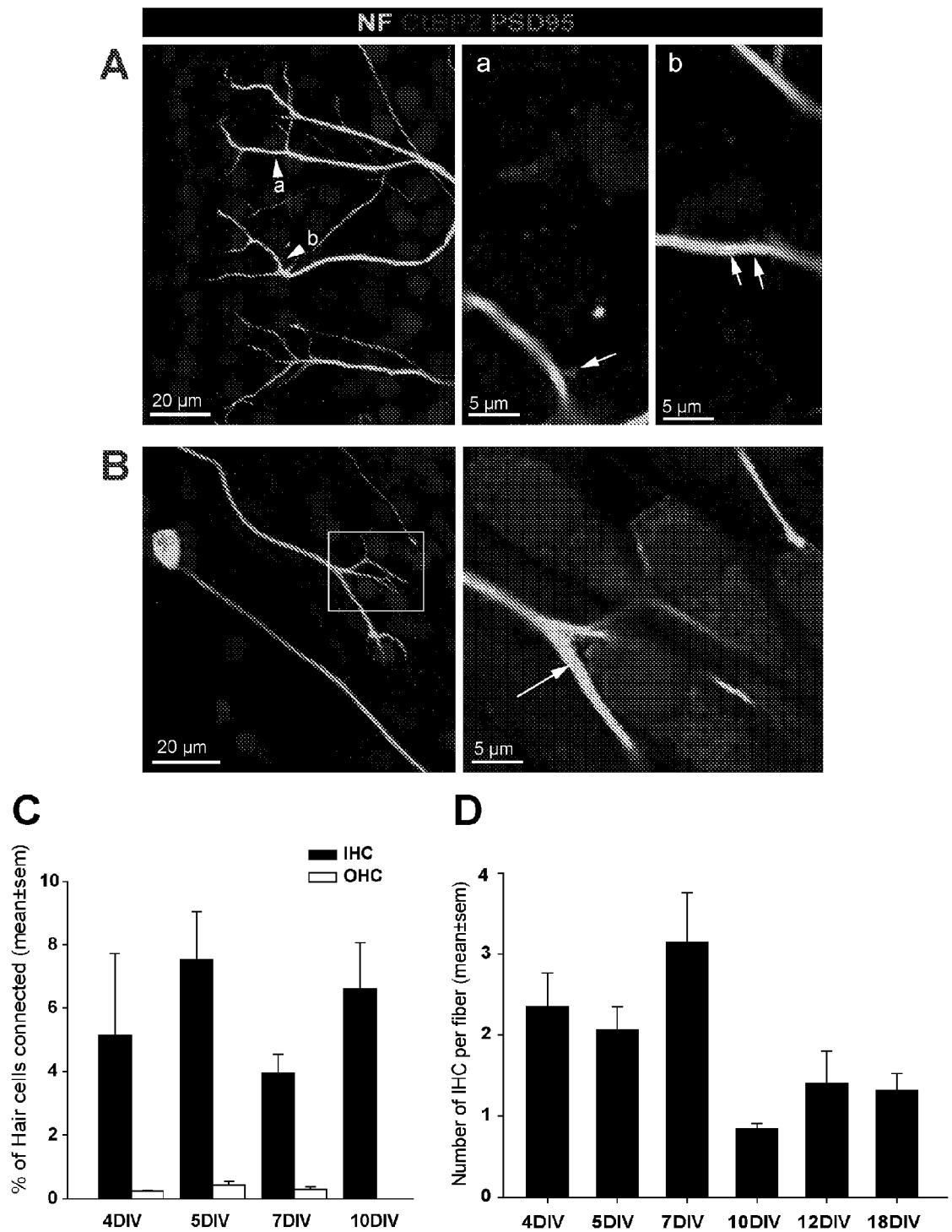
FIGS. 3A-D: Pruning of fibers in the inner hair cell and outer hair cell areas. A, B Hair cell synapses stained for neurofilament (green, original), PSD95 (red, original) and CtBP2 (blue, original). Arrows indicate double-stained synapses (PSD95 and CtBP2) in the outer (A) and inner (B) hair cell areas. Arrowheads (in A) indicate the areas (a and b) shown at higher power to the right. Box (in B) indicates area enlarged to the right. C, D Up to 8% of the hair cells, mostly inner hair cells, were contacted by spiral ganglion neurons after 4 to 10 days (C). Quantification of synapses indicated that the number of hair cells innervated by a single neuron decreased with increasing time in culture toward a value of 1.5 (D).

Pruning of Contacts Follows the In Vivo Pattern and is Enhanced by Inhibition of RGMa As can be seen in FIG. 3, branches of spiral ganglion neurons formed multiple synapses with inner and outer hair cells (FIGS. 3A, B). Individual fibers were followed by confocal imaging, and the number of hair cells contacted was quantified. Approximately 4-8% of inner hair cells were innervated and did not significantly increase with time in culture (4 DIV: $5.14\pm2.57$, n=108; 5 DIV: $7.54\pm1.51$, n=177; 7 DIV: $3.94\pm0.58$, n=45; 10 DIV: $6.61\pm1.44$, n=126) (n=inner hair cells counted; 4 separate experiments) while very few outer hair cells were innervated even after an extended time in culture (4 DIV: $0.24\pm0.01$, n=4; 5 DIV: $0.43\pm0.12$, n=32; 7 DIV: $2.28\pm0.09$, n=10) (n=outer hair cells counted: 4 separate experiments; FIG. 3C).

Branching of the fibers as they formed synapses was evaluated to determine how these networks matured. Branching was quantified after increasing intervals and the number of hair cells contacted by each fiber was found to decrease toward one after 18 days (4 DIV: $2.35\pm0.418$, n=107; 5 DIV: $2.06\pm0.28$, n=146; 7 DIV: $3.15\pm0.61$, n=28; 10 DIV: $0.84\pm0.07$, n=188; 12 DIV: $1.4\pm0.4$, n=11; 18 DIV: $1.31\pm0.21$, n=17) (n=inner hair cells counted; 4 separate experiments; FIG. 3D). These results demonstrate that the loss of synaptic contacts in culture might be similar to what occurs in vivo where the maturation of the initial innervation leads to a reduction in the number of synapses during development.

Figures 4A, 4B, 4C:
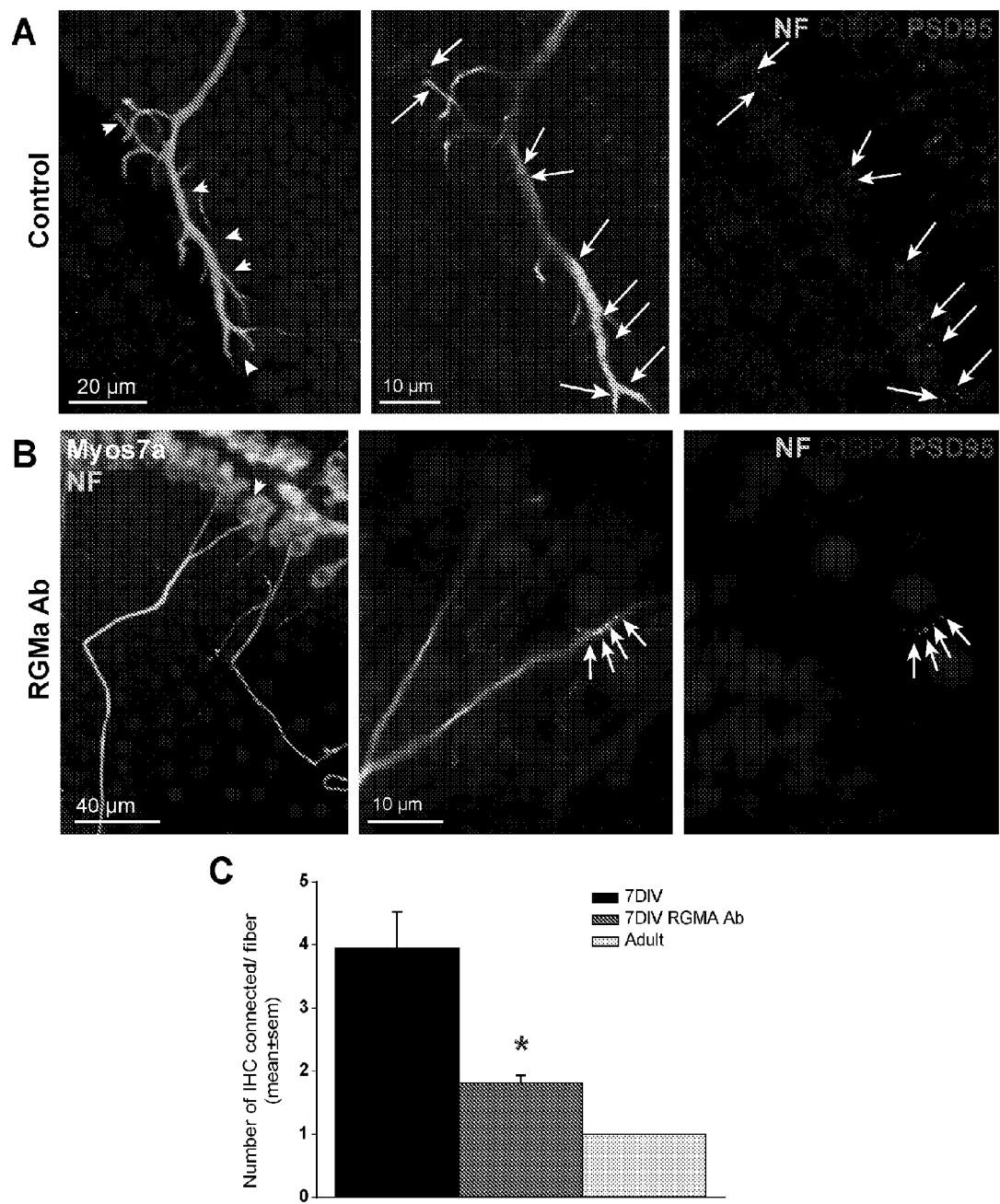
FIGS. 4A-C: Inhibition of RGMa increased the rate of pruning. A, B Spiral ganglion neurons added to the de-afferented organ of Corti were cultured for 7 days followed by labeling for neurofilament (green, original), PSD95 (red, original), CtBP2 (blue, original) and myosin VIIa (white, original). An increased rate of loss of branches was seen in cultures treated with RGMa antibody (B) compared to control (A). Innervation of the sensory epithelium at 7 days nearly reached the single hair cell innervation pattern of the adult (C). Asterisk indicates significance ($p<0.05$).

Treatment with the RGMa antibody accelerated the maturation of the branching toward the mature in vivo pattern (FIG. 4A). The number of inner hair cells connected by one fiber was decreased to nearly the native adult level after 7 days in culture. The number of hair cells contacted in cultures treated with RGMa antibody decreased to less than two inner hair cells (FIG. 4B) as compared to almost 4 in controls (FIG. 4C, respectively, 1.8±0.12, n=304 and 3.94±0.58, n=45) at the same time point (n=inner hair cells counted; 3 separate experiments).

Figure 5:
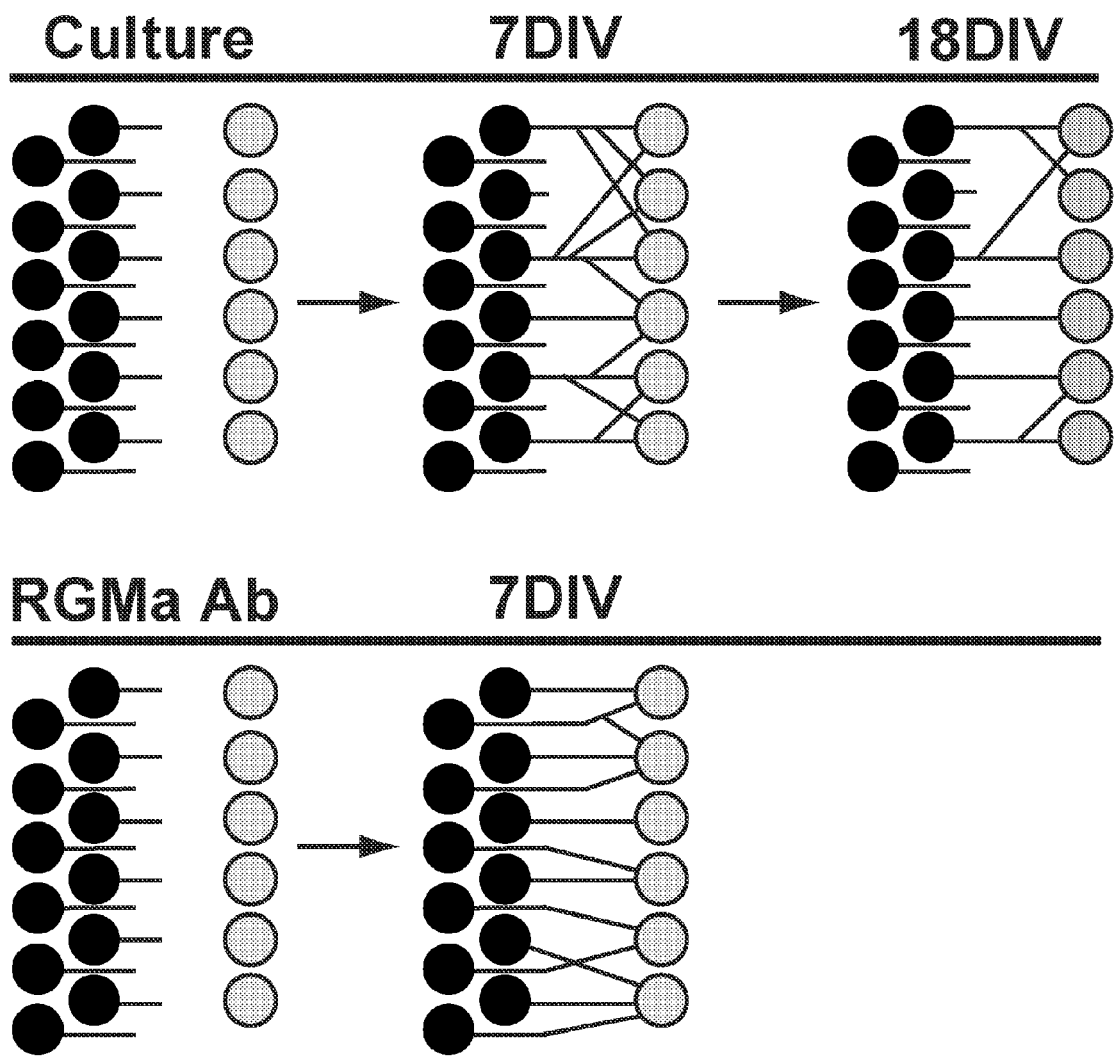
FIG. 5: Patterns of hair cell innervation mature with time in culture and were accelerated by blocking RGMa. Hair cells were initially innervated with multiple branches and refinement of the branching was observed with time in culture. Treatment with an antibody to RGMa increased the number of synapses and enhanced the rate of reduction in branches resulting in a pattern more like that of in vivo neurons.

As in the in the developing cochlea (Echteler (1992) Proc Natl Acad Sci USA 89:6324-6327; Huang et al. (2007) Development 134:2925-2933), contacts on multiple hair cells appeared to be pruned to yield single contacts from neuron to hair cell (FIG. 5). Spiral ganglion neurons contacted multiple inner hair cells or outer hair cells but never both. This result was interesting and suggested that signaling was inherent to the organ of Corti or the spiral ganglion neurons. The cochlea contains type I and type II spiral ganglion neurons that synapse, respectively, with inner and outer hair cells. The mechanism for this selectivity in culture is not certain but, without wishing to be bound by theory, could be due to a predetermined preference that directed the neurons to outer or inner hair cells or to an induced preference that restricted neurons to the hair cell type they first contacted. The former explanation is favored because the neurons often passed one type of hair cell en route to the other and because the ratio of inner hair cell to outer hair cell innervation (more than 10-fold higher with inner) was consistent with the in vivo ratio of the two neuronal types. This suggested that the neurons from newborn animals had identities as type I or II that remained intact after isolation and agrees with recent work suggesting that identity as a type I or II neurons is specified in the embryo (Koundakjian et al. (2007) J Neurosci 27:14078-14088) before contact with hair cells. Inhibition of RGMa enhanced the pruning and led to the mature branching pattern of the adult: the pattern was established sooner in the cultures treated with the antibody, and the final pattern was closer to that in the mature organ of Corti where neurons contact single hair cells (FIG. 5).

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of promoting or enhancing auditory neuron innervation of auditory hair cells, the method comprising administering to the neurons an effective amount of an inhibitor of Repulsive Guidance Molecule a (RGMa), wherein the inhibitor is an inhibitory antibody or antigen-binding portion thereof that binds specifically to RGMa.

2. A method of promoting or enhancing innervation of auditory hair cells in the inner ear of a subject in need thereof, the method comprising administering to the inner ear of the subject an effective amount of an inhibitor of RGMa, wherein the inhibitor is an inhibitory antibody or antigen-binding portion thereof that binds specifically to RGMa.

3. A method of treating a subject who has or is likely to have hearing loss or a balance disorder as a result of loss of or decrease in innervation of auditory hair cells, the method comprising administering to the inner ear of the subject an effective amount of an inhibitor of RGMa, wherein the inhibitor is an inhibitory antibody or antigen-binding portion thereof that binds specifically to RGMa.

4. The method of claim 1, wherein the inhibitory antibody or antigen-binding portion thereof is an Fab or F(ab')2.

5. The method of claim 1, further comprising administering one or more agents that promote the proliferation, differentiation, or survival or sensory neurons.

6. The method of claim 5, wherein the one or more agents are selected from the group consisting of caspase inhibitors, retinoic acid, Bone Morphogenetic Protein 4 (BMP4), anti-oxidants/Nrf2 activators, brain-derived neurotrophic factor (BDNF), neurotrophin 3 (NT3), and NT4/5.

7. The method of claim 2, wherein the subject has been or will be exposed to an ototoxic level of noise or to ototoxic agents such as radiation; antibiotics; chemotherapeutic agents; anti-inflammatory drugs; heavy metals; other known or suspected ototoxic agents; or aging.

8. The method of claim 3, wherein the inhibitory antibody or antigen-binding portion thereof is an Fab or F(ab')2.

9. The method of claim 3, further comprising administering one or more agents that promote the proliferation, differentiation, or survival or sensory neurons.

10. The method of claim 9, wherein the one or more agents are selected from the group consisting of caspase inhibitors, retinoic acid, Bone Morphogenetic Protein 4 (BMP4), anti-oxidants/Nrf2 activators, brain-derived neurotrophic factor (BDNF), neurotrophin 3 (NT3), and NT4/5.

11. The method of claim 3, wherein the subject has been or will be exposed to an ototoxic level of noise or to ototoxic agents such as radiation; antibiotics; chemotherapeutic agents; anti-inflammatory drugs; heavy metals; other known or suspected ototoxic agents; or aging.

12. The method of claim 1, the method further comprising administering one or more neural progenitor cells.

13. The method of claim 2, the method further comprising administering to the inner ear of the subject one or more neural progenitor cells.

14. The method of claim 3, the method further comprising administering to the inner ear of the subject one or more neural progenitor cells.

15. The method of claim 2, wherein the inhibitory antibody or antigen-binding portion thereof is an Fab or F(ab')2.

16. The method of claim 2, further comprising administering one or more agents that promote the proliferation, differentiation, or survival or sensory neurons.

17. The method of claim 16, wherein the one or more agents are selected from the group consisting of caspase inhibitors, retinoic acid, Bone Morphogenetic Protein 4 (BMP4), anti-oxidants/Nrf2 activators, brain-derived neurotrophic factor (BDNF), neurotrophin 3 (NT3), and NT4/5.

* * * * *

UNITED STATES PATENT AND TRADEMARK OFFICE
CERTIFICATE OF CORRECTION

PATENT NO. : 9,125,894 B2
APPLICATION NO. : 13/877356
DATED : September 8, 2015
INVENTOR(S) : Albert Edge Page 1 of 1

It is certified that error appears in the above-identified patent and that said Letters Patent is hereby corrected as shown below:

In the Specification

Column 1, Lines 17-21, delete "Government support under Grants Nos. R01 DC007174 and P30 DC05209 awarded by the National Institute on Deafness and other Communicative Disorders (NIDCD) of the National Institutes of Health. The Government has certain rights in the invention." and insert --Government support under Grant Numbers DC007174, DC005209 awarded by the National Institutes of Health. The government has certain rights in this invention.--

Signed and Sealed this
Thirteenth Day of April, 2021

Drew Hirshfeld
*Performing the Functions and Duties of the*
*Under Secretary of Commerce for Intellectual Property and*
*Director of the United States Patent and Trademark Office*